United States Patent [19]

Hetz et al.

[11] 4,291,578
[45] Sep. 29, 1981

[54] APPARATUS FOR ULTRASONIC SCANNING OF OBJECTS

[75] Inventors: Walter Hetz; Walter Derndinger, both of Erlangen, Fed. Rep. of Germany

[73] Assignee: Siemens Aktiengesellschaft, Berlin & Munich, Fed. Rep. of Germany

[21] Appl. No.: 46,700

[22] Filed: Jun. 8, 1979

[30] Foreign Application Priority Data

Jun. 15, 1978 [DE] Fed. Rep. of Germany ....... 2826277

[51] Int. Cl.³ ............................................. G01N 29/00
[52] U.S. Cl. ...................................... 73/633; 128/660
[58] Field of Search ................. 73/618, 619, 620, 621, 73/629, 633; 128/660

[56] References Cited

U.S. PATENT DOCUMENTS

| | | | |
|---|---|---|---|
| 3,924,452 | 12/1975 | Meyer et al. | 73/621 |
| 4,052,888 | 10/1977 | Brown et al. | 73/629 |
| 4,065,976 | 1/1978 | Taenzer | 73/633 |
| 4,196,630 | 4/1980 | Rudolph | 73/633 |

FOREIGN PATENT DOCUMENTS

| | | | |
|---|---|---|---|
| 1074211 | 1/1960 | Fed. Rep. of Germany . | |
| 1466873 | 9/1977 | Fed. Rep. of Germany . | |
| 1600873 | 9/1970 | France | 73/633 |

OTHER PUBLICATIONS

Compound Scanner "Combison", Kretztechnik, Austria, Fig. 6.

*Primary Examiner*—Stephen A. Kreitman
*Attorney, Agent, or Firm*—Hill, Van Santen, Steadman, Chiara & Simpson

[57] ABSTRACT

An ultrasonic-scan head is mounted by means of an articulated arm assembly; a swivel extension arm supports the assembly for rotation about a vertical central axis. Such vertical central axis is the isocenter for body sections to be scanned by the ultrasonic scan head. The construction of such an apparatus is desired which is particularly simple to handle during sectional plane selection. In particular, the apparatus mass to be moved is to be small so that a rotation of the entire scan system can also be conducted directly at the working location by the examining individual without requiring an assistant. This is achieved by virtue of the fact that the swivel extension arm, as the carrier for the articulated arm assembly, is coupled to a floor stand, and that the patient support can be arranged, preferably in a movably displaceable fashion, above the floor stand and above the extension arm which can be pivoted horizontally beneath said support so as to extend to either side of the support, or to an end of the support.

19 Claims, 5 Drawing Figures

APPARATUS FOR ULTRASONIC SCANNING OF OBJECTS

BACKGROUND OF THE INVENTION

The invention relates to an apparatus for ultrasonic scanning of objects, in particular, the human body, comprising an ultrasonic scan head which is mounted by means of a floor stand and an articulated arm, such that the scan head is rotatable along a path intersecting a vertical central axis which represents the isocenter for body sections to be scanned by the ultrasonic scan head pursuant to alignment of the articulated arm with the central axis.

In the case of known apparatus of this type, a base, which is movable by means of floor rollers, is the carrier of the articulated arm. The base, in turn, by means of a swivel extension arm, is coupled at the remote end of the extension arm to the object support (patient couch) such that it is rotatable about a vertical axis. The latter vertical axis, fixedly connected with the object support, is finally the central axis about which the entire base, together with the extension arm, must be moved on the floor rollers along a circular arc for the purpose of sectional plane rotation.

SUMMARY OF THE INVENTION

It is the object of the invention to produce an apparatus which in comparison to the above described apparatus, is simpler to handle in the case of sectional plane adjustment. In particular, the apparatus mass to be moved is to be kept as small as possible. Accordingly, a rotation of the entire scanning system should also be capable of being carried out directly, free of movement of the base while avoiding any tilting (or canting), by the examining individual at the work location (object support) without requiring an assistant.

The object is solved in accordance with the invention is that the swivel extension arm, as carrier for the articulated arm is coupled to a floor-fixed (stationary) central foot, as the base of the floor stand, such that the extension arm is rotatable about a vertical central axis passing through said central foot, and that the object support can be arranged, preferably movably displaceable, above the floor-fixed central foot and above the extension arm which is horizontally swingable beneath the support.

In the apparatus in accordance with the invention, the relatively heavy central foot is thus now fixed (or stationary) on the floor, and only the relatively light-weight arrangement of the articulated arm assembly on the swivel extension arm is now still rotated together with the scan head. It can be readily seen that the handling of the rotation is hereby greatly facilitated. It can be entirely conducted by the examining individual directly from the working location; i.e., seated position or standing position at the object support, without requiring an assistant.

In a preferred embodiment, such a rotation can be conducted by means of a hand drive; i,e., a hand wheel at the central axis of the swivel extension arm on the floor-stationary central foot. However, the rotation can just as well be effected by electric motor means; since only comparatively small masses need to be moved, the motors utilized to this end can be such having relatively low power which demand little space and which are cost-economical. The apparatus in accordance with the invention also permits, due to its simple handling, the rapid driving of the ultrasonic-scan head into a desired scan orientation. Thus, by this means, it is possible to switch over, e.g. from longitudinal sectional scanning guidance to transverse sectional scanning guidance, substantially more rapidly than hitherto. If, in addition, in an advantageous embodiment of the invention, the swivel extension arm is designed as a rotary to parallel motion converter; i.e., in the form of a parallelogram arm or an endless (continuous) band drive, or if the swivel extension arm comprises such a converter, the entire rotational movement of the swivel extension arm can be converted into mutually parallel linear steps, given random positions (or settings) for sectional scanning guidance of the ultrasonic scan head. The scanning of an object; for example, the human body in parallel sections which are capable of good reproduction (accurate repeatability) is hereby simplified in an optimum fashion.

Further advantages and details of the invention shall be apparent from the following description of an exemplary embodiment on the basis of the accompanying sheets of drawings in conjunction with the subclaims; and other objects, features and advantages will be apparent from this detailed disclosure and from the appended claims.

DETAILED DESCRIPTION

Figure 1:
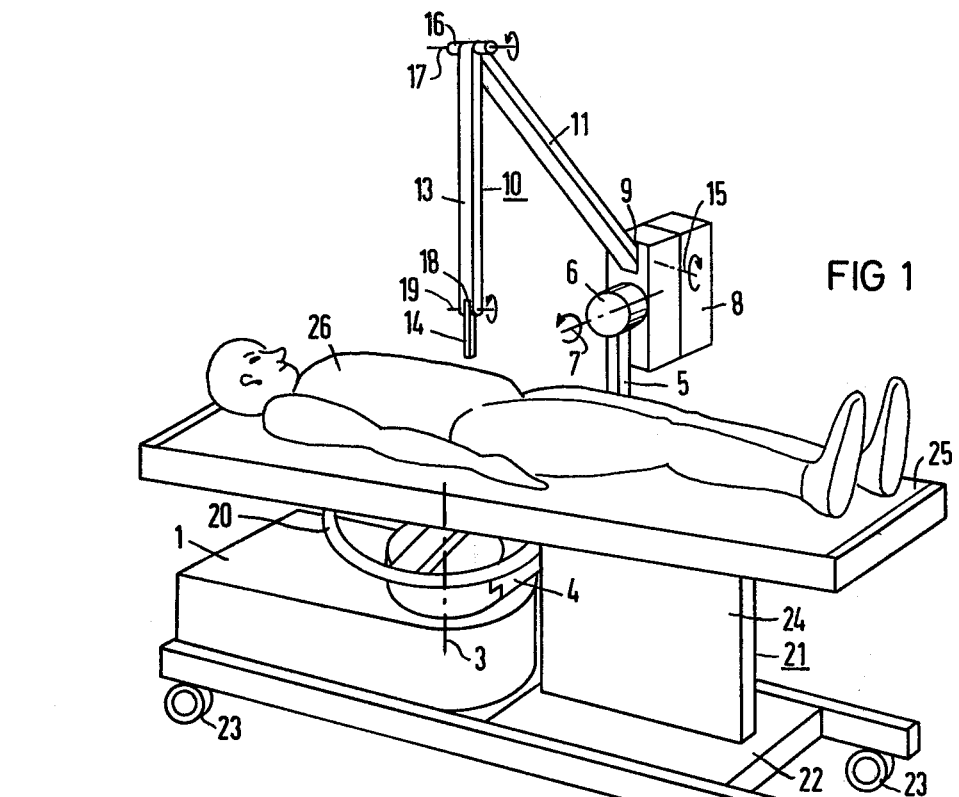
FIG. 1 illustrates an exemplary embodiment of the invention in a perspective view.

FIG. 1 illustrates, in a perspective view, a central foot 1 which stands fixedly on the floor 2 (FIG. 2) of the examination room. To this end, it can be non-displaceably connected with the floor, e.g. it can be screwed (or bolted) to the latter. Said central foot can likewise be virtually nondisplaceable solely on the basis of a correspondingly great weight which permits a displacement only with the application of great force. On the central foot 1, in a vertical central axis 3, a swivel extension arm 4 (only partially visible) is coupled so as to be rotatable about the central vertical axis. The swivel extension arm 4 is the carrier for a vertically adjustable lifting column 5 (likewise only partially visible) on whose upper end a box 8 is secured by means of a rotational mounting 6 such that it is capable of pivoting about a horizontal rotational axis 7. Projecting from an opening 9 of this box 8 is an articulated arm assembly 10 which consists of a first arm section 11 and a second arm section 13 and which serves as the carrier for an ultrasonic head 14. The ultrasonic head 14 is simultaneously designed as a handle for guiding the head together with the articulated arm over an examination area. The articulated arm assembly 10 manifests a total of three horizontal rotary joints of which the first for the box-side end of the first arm section 11 is disposed in the box 8. The rotational axis of this rotary joint is indicated in FIG. 1 by 15. A second rotary joint 16 with the rotational axis 17 interconnects the two arm sections 11 and 13. A rotary joint 18 with the rotational axis 19 at the lower end of the second arm 13 serves the purpose of accommodating horizontally swinging movement of the ultrasonic head 14. The entire arrangement of the articulated arm assembly 10 with box 8 and lifting column 5 on the swivel extension arm 4 can be rotated in a simple fashion about the vertical central axis 3 of the central foot 1 by means of hand wheel 20.

The ultrasonic-scan apparatus of FIG. 1 specifically serves the purpose of scanning the human body. For this reason, a driveable patient couch 21 is allocated to the central foot 1. The patient couch consists of the driveable carriage 22 with the rollers 23. Finally, on an intermediate member 24, the actual reclining platform 25 for patient 26 is mounted. The patient couch 21 can be pushed into interengagement with the central foot 1 in such a manner (e.g. also by means of additional horizontal displacement of the reclining platform 25 relative to the base 22), that the vertical central axis 3 of the central foot, in an imaginary extension through the reclining platform 25, penetrates the patient 26 in the region of the body parts to be examined; for example, the liver, heart, kidneys, or the like. The penetration point, upon orientation of the articulated arm assembly 10 with the central vertical axis 3, forms the isocenter for the body sections on the patient which are to be scanned by the ultrasonic scan head 14.

Figure 2:
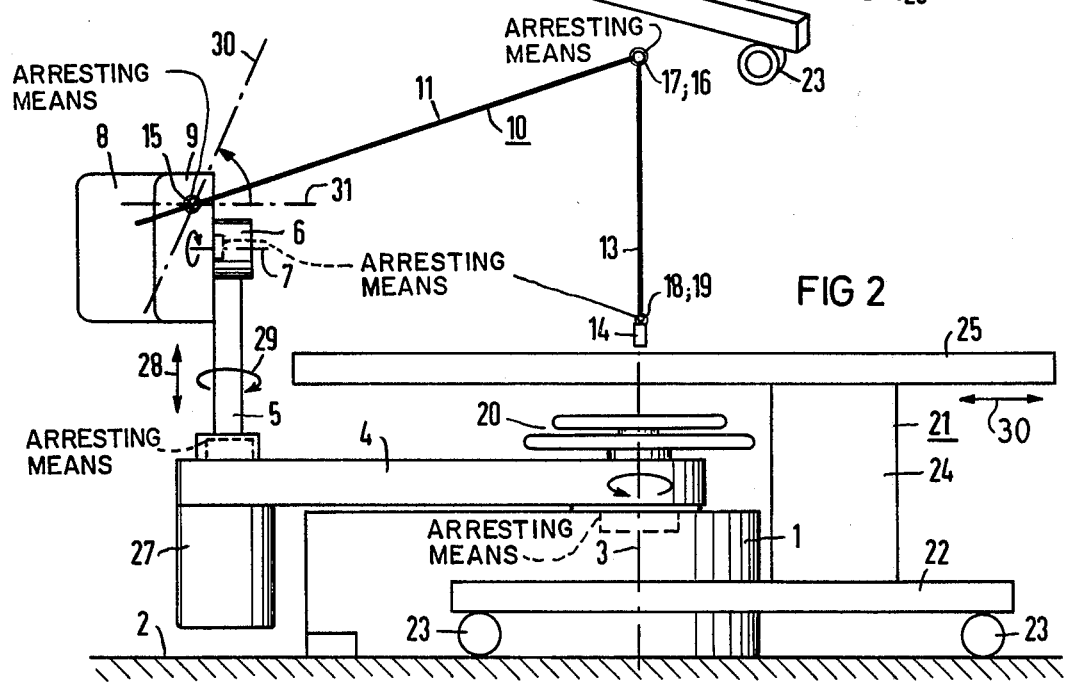
FIG. 2 illustrates the exemplary embodiment of FIG. 1 in a side view.

In FIG. 1, the swivel extension arm 4 together with the associated components 5, 6, 8, 10, is swung by means of the hand wheel 20, into a position in which the arm 10 together with the ultrasonic head 14 is aligned in a plane disposed transversely to the longitudinal axis of the patient 26. This position is the preferred position for scanning parallel cross-sections on the patient's body. FIG. 2 illustrates in a side view a further important position; namely, a rotated position, in which the articulated arm 10 together with the ultrasonic head 14 is in a plane essentially aligned in the longitudinal direction of the patient's body 26. This position serves the purpose of scanning of longitudinal sections. Of course, sectional scanning guidances to other random angular positions (about axis 3) between the transverse and longitudinal section are also possible.

In the lateral view of FIG. 2, the parts of the swivel extension arm 4, and of the lifting column 5, respectively, which are covered in the perspective view of FIG. 1, are better visible. Also, at the extreme end of the swivel extension arm 4, in the extension direction of the lifting carrier 5, the arrangement of a box 27 is recognizable. In this box there is disposed a drive for the longitudinal (vertical) displacement of the column 5 in the arrow directions 28 (and, if desired, also a rotary drive for rotating the column 5 in the direction of the rotational arrow 29). In addition, the maximum deflection positions of the first arm section 11 of the swivel arm 10, resulting, respectively, in engagement with the edges of the opening 9, are indicated on the box 8 for the support arm 10 with the identifying numbers 30, and 31, respectively. The articulated arm 10 is, of course, equilibrated or counterbalanced as to the arm section 11 (and also as to arm section 13) for every height and swivel position.

Thus, in the exemplary embodiment of FIGS. 1 and 2, if the patient's body 26 to be examined is supported over the central vertical axis 3, and if the horizontal axis 7 is adjusted in height and direction to the location of the patient's body to be examined through a corresponding swiveling of the lifting column 5 by means of pushing the articulated arm assembly 10 (or by means of actuation of a rotary motor), then sectional planes through the patient's body can be scanned by means of the articulated arm assembly 10 with the sonic head 14 which sectional planes, even in the case of rotation of the entire system about the central vertical axis 3, or also in the case of swiveling the articulated arm assembly 10 with the sonic head 9 about the horizontal axis 7, always intersect at the central axis 3. Accordingly, the central axis 3 is the isocenter for all scanned body sections.

Via the rotatable and height-adjustable lifting column 5, by means of a suitable rotary to parallel motion converter, e.g. by constructing the swivel extension arm as a parallelogram arm or arranging an endless belt drive in the swivel extension arm, a parallel, horizontal forced (or compulsory) guidance of the articulated arm assembly with the sonic head 14 can be achieved. In this instance, the entire rotational movement of the swivel extension arm 4, given random positions—for the purpose of sectional scanning guidance—of the ultrasonic-scan head 14 relative to the object support 25, is converted into mutually parallel linear steps. Thus, the scanning of the patient's body 26 is rendered possible in a simple fashion in parallel sections which are capable of good reproduction (accurate repeatability). The vertical height adjustment of the lifting column 5 additionally also permits the parallel vertical guidance of the articulated arm assembly 10 with sonic head 14 for the purpose of scanning parallel sectional planes during vertical scanning or during scanning which is inclined to the horizontal. The position determination (or detection) of all movements for the sectional plane representation on a video apparatus; for example, an oscilloscope tube, proceeds as conventionally via translation- or rotation-indicators pursuant to electronic processing of the data.

Figure 3:
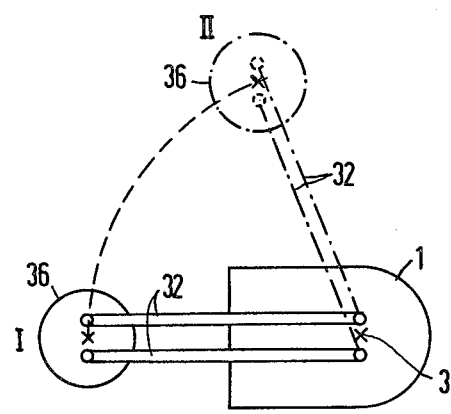
FIG. 3 illustrates the design of the swivel extension arm as a parallelogram arm.

FIG. 3 illustrates the design of the swivel extension arm as a parallelogram arm 32 in two swivel positions I and II.

Figure 4:
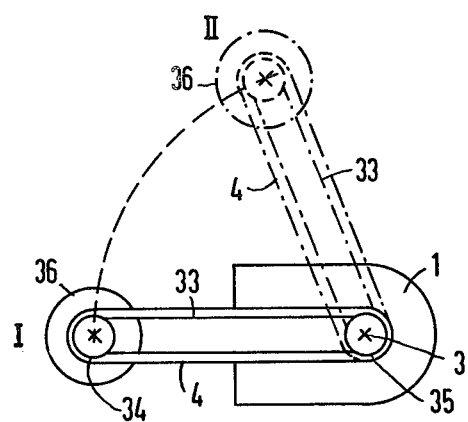
FIG. 4 illustrates the design of the swivel extension arm as an endless band drive.

Correspondingly, FIG. 4 illustrates a modification to the extent that there is arranged in the swivel extension arm 4 an endless loop (band) drive with chain or belt 33 and drive rollers 34 and 35, respectively. Two swivel positions are again indicated with I and II. The identifying number 36 comprises an articulated arm together with an ultrasonic scan head and a box in schematic representation.

Figure 5:
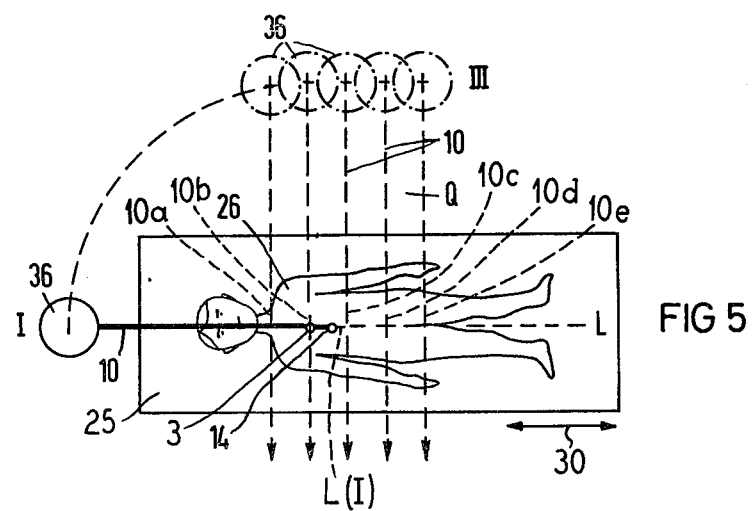
FIG. 5 is a diagrammatic plan view illustrating a switching-over from longitudinal scanning to transverse scanning in mutually parallel sectional planes.

FIG. 5 finally, illustrates in plan view the swingover from scanning in longitudinal section L in the position I to cross-sectional scanning Q in exemplary positions III with designs of the swivel extension arm according to FIGS. 3 and 4, the patient support 25 remaining stationary and the swivel extension arm 32 or 4 assuming successive angular positions about vertical central axis 3 to provide scanning in the successive scanning planes such as 10a, 10b, FIG. 5 (corresponding to successive planes occupied by arm assembly 10 in FIG. 5). Further scanning planes can be selected by longitudinal movement of patient support 25, for example, if swiveling motion is limited by member 24, FIG. 2.

It will be apparent that many modifications and variations may be effected without departing from the scope of the novel concepts and teachings of the present invention.

Each of the illustrated embodiments may be provided with arresting means (as diagrammatically indicated in FIG. 2) such as for example magnetic brakes in the individual rotational joints such as indicated between 1 and 4 by vertical axis 3, such as represented between components 4 and 5 by directional arrows 28 and 29, and such as represented by the axes 7 and 15 between lifting column 5 and arm segment 11, and such as indicated by axes 17 and 19 between components 11 and 13, and 13 and 14. By selective operation of the various individual arresting means, the scanning system can be placed in a desired position so as to effect scanning along a desired scanning path configuration such as the scanning path configurations indicated at 10a and 10b in FIG. 5.

The support platform 25 may be longitudinally movable by means of a motor in a manner known per se as indicated by arrow 30, FIG. 2, in a horizontal plane while the base 22 of the support 21 is in fixed relation to the floor stand 1 as shown in FIGS. 1 and 2. Such longitudinal positioning of the support platform 25 would provide for selective scanning along scanning path configurations such as indicated at 10c, 10d, and 10e, as well as along longitudinal scanning path configurations such as indicated at L(I) in the longitudinal plane L, FIG. 5.

We claim as our invention:

1. Apparatus for ultrasonic scanning of objects, in particular, the human body, comprising a floor stand having a central vertical axis, an ultrasonic scan head, an articulated arm assembly carrying the scan head, an object support for supporting an object to be scanned, the scan head being operative to effect scanning along certain scanning path configurations based on alignment of the articulated arm assembly with the central vertical axis, an extension arm (4) supporting the articulated arm assembly (10) and being coupled to the floor stand (1), said extension arm being rotatable about said vertical central axis (3) which passes through said floor stand, and said object support (25) being arranged above the floor stand (1) and above the extension arm (4) such that the extension arm is capable of being swung horizontally beneath said support with the central vertical axis being in alignment with the object support and defining an isocenter for the certain scanning path configurations of the scan head, the extension arm (4) comprising a rotary-parallel motion converter said motion converter comprising a parallelogram arm (32).

2. Apparatus for ultrasonic scanning of objects, in particular, the human body, comprising a floor stand having a central vertical axis, an ultrasonic scan head, an articulated arm assembly carrying the scan head, an object support for supporting an object to be scanned, the scan head being operative to effect scanning along certain scanning path configurations based on alignment of the articulated arm assembly with the central vertical axis, an extension arm (4) supporting the articulated arm assembly (10) and being coupled to the floor stand (1), said extension arm being rotatable about said vertical central axis (3) which passes through said floor stand, and said object support (25) being arranged above the floor stand (1) and above the extension arm (4) such that the extension arm is capable of being swung horizontally beneath said support with the central vertical axis being in alignment with the object support and defining an isocenter for the certain scanning path configurations of the scan head, the extension arm (4) comprising a rotary-parallel motion converter said motion converter comprising an endless loop band drive (33, 34, 35).

3. Apparatus for ultrasonic scanning of objects, in particular, the human body, comprising a floor stand having a central vertical axis, an ultrasonic scan head, an articulated arm assembly carrying the scan head, an object support for supporting an object to be scanned, the scan head being operative to effect scanning along certain scanning path configurations based on alignment of the articulated arm assembly with the central vertical axis, an extension arm (4) supporting the articulated arm assembly (10) and being coupled to the floor stand (4), said extension arm being rotatable about said vertical central axis (3) which passes through said floor stand, and said object support (25) being arranged above the floor stand (1) and above the extension arm (4) such that the extension arm is capable of being swung horizontally beneath said support with the central vertical axis being in alignment with the object support and defining an isocenter for the certain scanning path configurations of the scan head, the extension arm (4) together with the articulated arm assembly (10) and the ultrasonic scan head (14) being rotatable about the central vertical axis (3) by means of a hand drive, a hand wheel (20) rotatable about the central vertical axis (3) and coupled with said extension arm (4) for effecting rotation of the extension arm (4) together with the articulated arm assembly (10) and the ultrasonic scan head (14) about the central vertical axis (3).

4. Apparatus for ultrasonic scanning of objects, in particular, the human body, comprising a floor stand having a central vertical axis, an ultrasonic scan head, an articulated arm assembly carrying the scan head, an object support for supporting an object to be scanned, the scan head being operative to effect scanning along certain scanning path configurations based on alignment of the articulated arm assembly with the central vertical axis, an extension arm (4) supporting the articulated arm assembly (10) and being coupled to the floor stand (1), said extension arm being rotatable about said vertical central axis (3) which passes through said floor stand, and said object support (25) being arranged above the floor stand (1) and above the extension arm (4) such that the extension arm is capable of being swung horizontally beneath said support with the central vertical axis being in alignment with the object support and defining an isocenter for the certain scanning path configurations of the scan head, arresting means for preventing rotation at respective individual joints of the articulated arm assembly for the purpose of determining a scanning path configuration for the scan head, said arresting means comprising magnetic brakes at the joints of the articulated arm assembly for the purpose of fixing the articulated arm assembly to provide for a specific scanning path configuration of the scan head.

5. Apparatus for ultrasonic scanning of objects, in particular the human body, comprising a floor stand (1) having a vertical axis (3), an ultrasonic scan head (14), an articulated arm assembly (10) carrying the scan head, an object support assembly (21) having an object support (25) for supporting an object to be scanned, the scan head being operative to effect scanning along certain scanning path configurations based on positioning of the articulated arm assembly (10) relative to a central scanning axis intersecting the object support (25), an extension arm (4) supporting the articulated arm assembly (10) and being coupled to the floor stand (1), said object support (25) being arranged above the floor stand (1) and above the extension arm (4), said extension arm (4) being pivotally mounted by said floor stand (1) for rotation about said vertical axis (3) of said floor stand (1) with said vertical axis (3) coinciding with the central scanning axis and defining an isocenter for the certain scanning path configurations of the scan head, said floor stand (1) being in a stationarily fixed position beneath said object support (25) and resting on a floor surface, and being separate from said object support (25), said floor stand (1) and said object support assembly (21) being of cooperating configuration to accommodate movement of the object support (25) while said object support (25) is in overlying relation to said floor stand (1) and while said floor stand (1) remains in said stationarily fixed position on the floor surface, and said object support (25) being movable so as to position said vertical axis (3) of said floor stand (1) in vertical alignment with a desired region of said object support (25).

6. Apparatus according to claim 5, with said extension arm (4) comprising a rotary-parallel motion converter.

7. Apparatus according to claim 6, with said motion converter comprising a parallelogram arm (32).

8. Apparatus according to claim 6, with said motion converter comprising an endless loop band drive (33, 34, 35).

9. Apparatus according to claim 6, with said motion converter being operable to convert the entire rotational movement of the extension arm (4) about the vertical axis (3) such that the ultrasonic scan head (14) is successively offset for scanning along scanning paths (10a, 10b) which are mutually parallel.

10. Apparatus according to claim 9, with means (5) providing for rotation (29) of the ultrasonic scan head (14) about a vertical axis offset from said vertical axis (3).

11. Apparatus according to claim 5, with a hand drive coupled with the extension arm (4) and via the extension arm being coupled with the articulated arm assembly (10) and the ultrasonic scan head (14) for effecting rotation thereof about the vertical axis (3).

12. Apparatus according to claim 11, with a hand wheel (20) rotatable about the vertical axis (3) and coupled with said extension arm (4) for effecting rotation of the extension arm (4) together with the articulated arm assembly (10) and the ultrasonic scan head (14) about the vertical axis (3).

13. Apparatus according to claim 5, with a lifting column (5) supporting the articulated arm assembly (10) and the ultrasonic scan head (14) and in turn supported on the extension arm (4) for the purpose of driving the articulated arm assembly together with the ultrasonic scan head to different height positions.

14. Apparatus according to claim 13, with said lifting column (5) being operable to drive said articulated arm assembly together with the ultrasonic scan head between initial height position and a final height position to produce a scanning movement of the ultrasonic scan head.

15. Apparatus according to claim 13, characterized with the lifting column (5) being rotatable about its vertical longitudinal axis to provide for rotation of the articulated arm assembly about said vertical longitudinal axis.

16. Apparatus according to claim 5, with arresting means for preventing rotation at respective individual joints of the articulated arm assembly for the purpose of determining a scanning path configuration for the scan head.

17. Apparatus according to claim 16, with said arresting means comprising magnetic brakes at the joints of the articulated arm assembly for the purpose of fixing the articulated arm assembly to provide for a specific scanning path configuration of the scan head.

18. Apparatus according to claim 5, with the object support assembly (21) comprising a base (22) supporting said object support (25), and said object support being longitudinally shiftable relative to the base.

19. Apparatus according to claim 18, with said object support (25) being mobile in a horizontal plane relative to the base (22) while the base (22) remains fixed relative to the floor stand (1).

* * * * *